US008034586B2

(12) United States Patent
Broekaert et al.

(10) Patent No.: US 8,034,586 B2
(45) Date of Patent: Oct. 11, 2011

(54) METHOD FOR MAKING SOLUBLE ARABINOXYLANS AS CO-PRODUCT OF FERMENTATION OF WHOLE-GRAIN CEREALS (75) Inventors: Willem Broekaert, Dilbeek (BE); Christophe Courtin, Wilsele (BE); Jan Delcour, Heverlee (BE)

(73) Assignee: Fugeia NV (BG)

( * ) Notice: Subject to any disclaimer, the term of this patent is extended or adjusted under 35 U.S.C. 154(b) by 248 days.

(21) Appl. No.: 12/306,943

(22) PCT Filed: Jul. 2, 2007

(86) PCT No.: PCT/BE2007/000072
§ 371 (c)(1),
(2), (4) Date: Sep. 8, 2009

(87) PCT Pub. No.: WO2008/000050
PCT Pub. Date: Jan. 3, 2008

(65) Prior Publication Data
US 2010/0035302 A1    Feb. 11, 2010

(30) Foreign Application Priority Data

Jun. 30, 2006  (GB) .................................. 0612976.1

(51) Int. Cl.
*C12P 19/00*  (2006.01)
*C12P 7/06*  (2006.01)
(52) U.S. Cl. ........................................ 435/72; 435/161
(58) Field of Classification Search .................. None
See application file for complete search history.

(56) References Cited

FOREIGN PATENT DOCUMENTS

| JP | 04309501 A | 11/1992 |
| JP | 4309501 A | 11/1992 |
| JP | 05112455 A | 5/1993 |
| JP | 5112455 A | 5/1993 |
| JP | 10237107 A | 9/1998 |
| WO | WO 97/27293 A1 | 7/1997 |
| WO | WO 02/067698 | 9/2002 |
| WO | WO 02/067698 A1 | 9/2002 |

OTHER PUBLICATIONS

Caprita et al., "Biochemical Aspects of Non-Starch Polysaccharides," *Scientific Papers: Animal Science and Biotechnologies* 43:368-375, 2010.
Communication from Examiner for GB Application No. 0612976.1, dated Nov. 1, 2006.
E-mail Communication between Joël Bazin of Novozymes France S.A. and Joseph Fockedey of Cosucra Groupe Warcoing and its English translation, dated Sep. 1, 2010 and Sep. 6, 2010.
Fastinger, "Development of a Novel Value-Added Distillers Dried Grains with Solubles: Effects on Amino Acid and Energy Digestibility in Pigs," Dissertation, Ohio State University, 2005.
Faulds et al., "Specificity of Feruloyl Esterases for Water-Extractable and Water-Unextractable Feruloylated Polysaccharides: Influence of Xylanase," *Journal of Cereal Science* 38:281-288, 2003.
International Preliminary Report on Patentability for PCT/BE2007/000072, mailed Jan. 15, 2009.
International Search Report and Written Opinion for PCT/BE2007/000072, mailed Jan. 29, 2008.
Grootaert et al., "Microbial Metabolism and Prebiotic Potency of Arabinoxylan Oligosaccharides in the Human Intestine," *Trends in Food Science & Technology* 18:64-71, 2007.
Maes et al., "Relative Activity of two Endoxylanases Towards Water-Unextractable Arabinoxylans in Wheat Bran," *Journal of Cereal Science* 39:181-186, 2004.
Moers et al., "Endoxylanase Substrate Selectivity Determines Degradation of Wheat Water-Extractable and Water-Unextractable Arabinoxylan," *Carbohydrate Research* 340:1319-1327, 2005.
Search Report for GB Application No. 0612976.1, mailed Oct. 30, 2006, date of search Oct. 27, 2006.
Sorensen et al., "Efficiencies of Designed Enzyme Combinations in Releasing Arabinose and Xylose from Wheat Arabinoxylan in an Industrial Ethanol Fermentation Residue," *Enzyme and Microbial Technology* 36:773-784, 2005.
Sørensen et al., "Optimization of Reaction Conditions for Enzymatic Viscosity Reduction and Hydrolysis of Wheat Arabinoxylan in an Industrial Ethanol Fermentation Residue," *Biotechnol. Prog.* 22:505-513, 2006.
Swennen et al., "Large-Scale Production and Characterisation of Wheat Bran Arabinoxylooligosaccharides," *J. Sci. Food Agric.* 86:1722-1731, 2006.
Official Communication from European Patent Office for European Patent Application 07 784 889.3, dated Dec. 9, 2010.
Grootaert et al., "Microbial Metabolism and Prebiotic Potency of Arabinoxylan Oligosaccharides in the Human Intestine," *Trends in Food Science & Technology*, 18: 64-71, 2007.
Maes et al., "Relative Activity of Two Endoxylanases Towards Water-Unextractable Arabinoxylans in Wheat Bran," *Journal of Cereal Science*, 39: 181-186. 2004.
Moers et al., "Endoxylanase Substrate Selectivity Determines Degradation of Wheat Water-Extractable and Water-Unextractable Arabinoxylan," *Carbohydrate Research*, 340: 1319-1327, 2005.
Sørensen et al., "Efficiencies of Designed Enzyme Combinations in Releasing Arabinose and Xylose from Wheat Arabinoxylan in an Industrial Ethanol Fermentation Residue." *Enzyme and Microbial Technology*, 36: 773-784, 2005.
Sørensen et al., "Optimization of Reaction Conditions for Enzymatic Viscosity Reduction and Hydrolysis of Wheat Arabinoxylan in an Industrial Ethanol Fermentation Residue," *Biotechnology Progress*, 22: 505-513, 2006.
Swennen, "Large-Scale Production and Characterisation of Wheat Bran Arabinoxylooligosaccharides," *Journal of the Science of Food and Agriculture*, 86: 1722-1731, 2006.
Search Report for British Application No. GB0612976.1, dated Oct. 30, 2006.
Supplemental Search Report for British Application No. GB0612976.1, dated Nov. 1, 2006.

(Continued)

*Primary Examiner* — Herbert J. Lilling
(74) *Attorney, Agent, or Firm* — Clark & Elbing LLP (57) ABSTRACT

The present invention provides a method for producing preparations comprising soluble arabinoxylans as co-products of ethanol production through fermentation of whole-grain cereals. The method results in preparations that are highly enriched in soluble arabinoxylans, which can be used as a food, beverage, or feed ingredients.

17 Claims, 4 Drawing Sheets

OTHER PUBLICATIONS

International Search Report for International Application PCT/BE2007/000072, mailed Jan. 29, 2008.

Written Opinion for International Application PCT/BE2007/000072, mailed Jan. 29, 2008.

International Preliminary Report on Patentability and Written Opinion (PCT/BE2007/000072) mailed Jan. 15, 2009.

Office Action for European Patent Application No. EP 07 784 889.3, dated Jun. 24, 2009.

SEQUENCE LISTING

<160> NUMBER OF SEQ ID NOS: 1

<210> SEQ ID NO 1
<211> LENGTH: 190
<212> TYPE: PRT
<213> ORGANISM: Hypocrea jecorina

<400> SEQUENCE: 1

```
Gln Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60
```

-continued

```
Ser Tyr Asn Pro Asn Gly Asn Ser Tyr Leu Ser Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
            165                 170                 175

Glu Gly Tyr Phe Ser Ser Gly Ser Ala Ser Ile Thr Val Ser
            180                 185                 190
```

METHOD FOR MAKING SOLUBLE ARABINOXYLANS AS CO-PRODUCT OF FERMENTATION OF WHOLE-GRAIN CEREALS

CROSS-REFERENCE TO RELATED APPLICATIONS

This application is the U.S. National Stage of International Application No. PCT/BE2007/000072, filed Jul. 2, 2007, which, in turn, claims the benefit of British Patent Application No. 0612976.1, filed Jun. 30, 2006.

FIELD OF THE INVENTION

The present invention relates to a method for producing preparations comprising soluble arabinoxylans as co-products of ethanol production through fermentation of whole-grain cereals. The method results in preparations that are highly enriched in soluble arabinoxylans, which can be used as a food, beverage, or feed ingredients.

BACKGROUND OF THE INVENTION

Ethanol is widely used in potable alcoholic beverages, as a solvent for extraction or chemical synthesis, or as a fuel additive or straight fuel. Alcohol is mainly produced through fermentation by yeast of plant-derived material that is rich in carbohydrates. Starch-rich grains of cereals, including but not limited to wheat, corn, barley, rye, rice, oats, triticale, spelt, sorghum, or pearl millet, can be used as a starting material for ethanol production. The processing of cereals for ethanol production generates co-products, such as for instance dried distillers grain and solubles (DDGS), which are used as low-value animal feed or burned to recover heat energy. There is a need for diversification of the co-products of ethanol production, especially co-products with a high added value.

Figure 1:
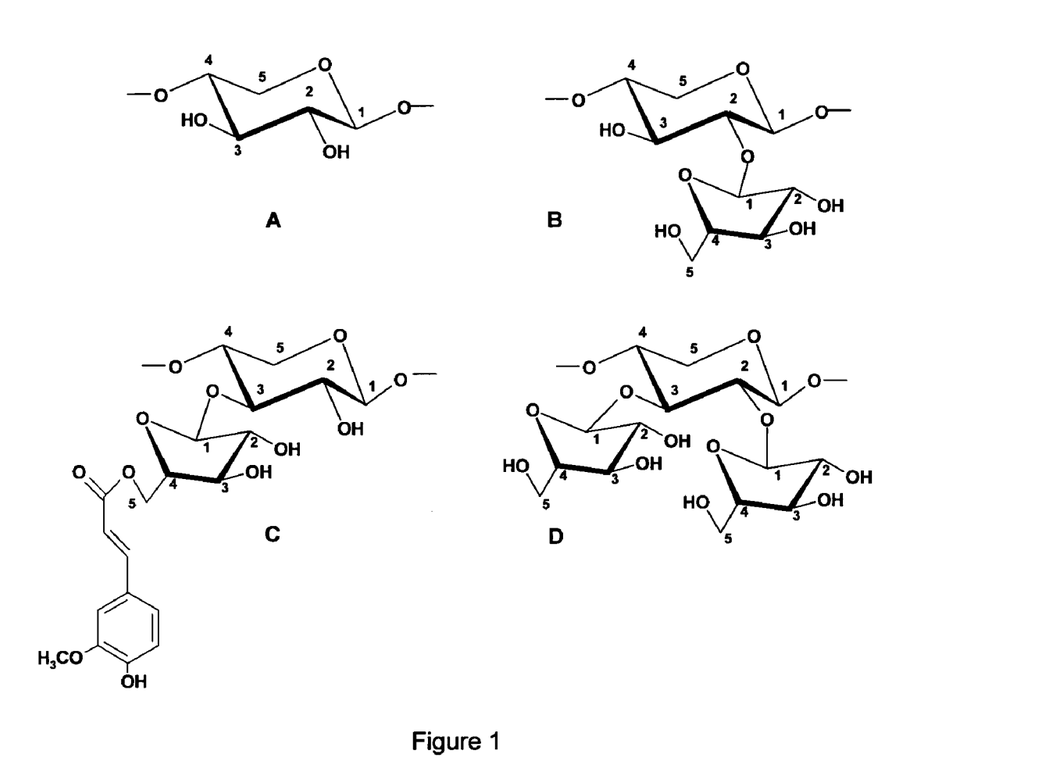
FIG. 1: Structural elements of arabinoxylans. A: unsubstituted β-D-xylopyranosyl residue. B: β-D-xylopyranosyl residue substituted at O-2 with an α-L-arabinofuranosyl moiety. C: β-D-xylopyranosyl residue substituted at O-3 with an α-L-arabinofuranosyl moiety. D: β-D-xylopyranose residue substituted at O-2 and O-3 with α-L-arabino-furanosyl moieties. Structure C shows the linkage of ferulic acid to O-5 of an α-L-arabinofuranosyl residue.

Cereals contain 5-10% of arabinoxylan, which together with starch, cellulose and β-glucan constitute the most abundant cereal carbohydrates. Arabinoxylan comprises a main chain of β-1,4-linked D-xylopyranosyl units to which O-2 and/or O-3 α-L-arabino-furanosyl units are linked (Gruppen et al. 1992). In a typical arabinoxylan, unsubstituted, mono-substituted and disubstituted xylose residues occur (see FIG. 1). In addition, the arabinose side chains can be covalently linked to acetyl, methylglucuronic acid, or feruloyl substituents, the latter being capable to form ferulic acid dimer cross-links. Arabinoxylans in cereals are either water-extractable or water-unextractable (Gruppen et al. 1992; Courtin and Delcour, 2001). Water-unextractable arabinoxylans (WU-AX) can be partially solubilised under alkaline conditions or by using enzymes, such as endoxylanases. WU-AX bind large amounts of water. The water-extractable arabinoxylans (WE-AX) have very high molecular masses (up to 800,000 Dalton) depending on the source and extraction method, and have an extraordinary viscosity forming potential. Arabinoxylans can not be fermented by standard strains of the yeast *Saccharomyces cerevisiae*, and therefore do not contribute to the production of ethanol by fermentation of cereals.

Arabinoxylo-oligosaccharides (AXOS), oligosaccharides derived from arabinoxylan, have been shown to exert prebiotic properties and could therefore be an interesting co-product of ethanol production. Prebiotics are compounds, usually non-glucosidic oligosaccharides, that can not be digested by enzymes of the upper gastro-intestinal tract but are fermented selectively by some types of intestinal bacteria in the large intestine (Gibson and Roberfroid, 1995; Roberfroid, 1988; Van Loo, 2004). The presence of prebiotics in the diet causes a shift in the composition of the intestinal bacterial population, typically characterised by a relative increase in *Lactobacillus* and *Bifidobacterium* species. This shift in the microbiota of the intestine is associated with improved overall health, reduced gut infections, increased levels of intestinal short chain fatty acids, better absorption of minerals, and suppression of colon cancer initiation (Van Loo, 2004). A preparation consisting predominantly of AXOS with a degree of polymerisation (DP) of 3-5 (arabinosylxylobiose, arabinosylxylotriose, arabinosylxylotetraose, and diarabinosylxylotetraose) has been shown to exert prebiotic effects and to increase the levels of Bifidobacteria in the intestines of rats and mice (Yamada et al., 1993). It has further been demonstrated that AXOS preparations with an average DP ranging between 5 and 50 have particularly strong prebiotic properties, as evidenced by tests performed on chickens, rats and humans (WO06/002495). AXOS have also been shown to improve the growth performance and food utilisation of monogastric animals (WO03/015533). AXOS-containing preparations can therefore find wide uses as ingredients for food, beverage and feed products.

Up to now no economically viable method for the production of AXOS has been developed. The method developed by Yamada et al. (1993) involves chemical extraction of arabinoxylan using a concentrated alkaline solution, followed by neutralisation, removal of the salts, enzymic hydrolysis with endoxylanase, and chromatography on a carbon column (Yamada et al., 1993). The main drawback of this method is that the alkaline extraction of arabinoxylan is environment-unfriendly, and requires costly removal of the minerals by extensive dialysis or ultrafiltration before enzymic hydrolysis can be performed. Another method to produce AXOS involves hydrothermal autohydrolysis of hardwood or brewery spent grain. In this method a suspension of plant material is heated in a special reactor at 150-190° C. for 20-60 min (EP 0265970B1; Kabel et al., 2002; Carvalheiro et al., 2004). The drawback of this method is that, due to the high reaction temperature, side products are produced that are undesirable for food purposes, such as furfural, hydroxymethylfurfural and levulinic acid (Carvalheiro et al., 2004). Other methods have used endoxylanase enzymes to solubilise AXOS from WU-AX, in particular from cereal bran which is known to be rich in WU-AX (Delcour et al. 1999). Several related procedures have been described in which bran is first treated with an alpha amylase to convert starch in soluble maltodextrins, whereafter AXOS is released from the insoluble fraction through the action of endoxylanase (Maes et al 2004; Swennen et al. 2006; WO2006/027529). Patent US2002/0037331 teaches a method to extract AXOS from bran consisting of extrusion followed by treatment with endoxylanase and amylase, further followed by ultrafiltration. The drawback of bran-based methods are the relatively low recovery of AXOS and the low value of the abundantly generated co-products. The present invention provides a method allowing the co-production of AXOS in an ethanol production process using arabinoxylan-containing cereal material as feedstock. The method according to the present invention comprises the exposure of the cereal material to an appropriate endoxylanase enzymatic activity in order to solubilise a substantial portion of the water-unextractable arabinoxylans comprised therein. The co-production of ethanol and AXOS has the advantage that it allows a more efficient use of the infrastructure, energy input and raw materials, while providing an AXOS preparation suitable for use as a food or animal feed additive. Moreover, the co-production of AXOS according to the present invention has no negative impact on the yield of the ethanol production.

Figure 2:
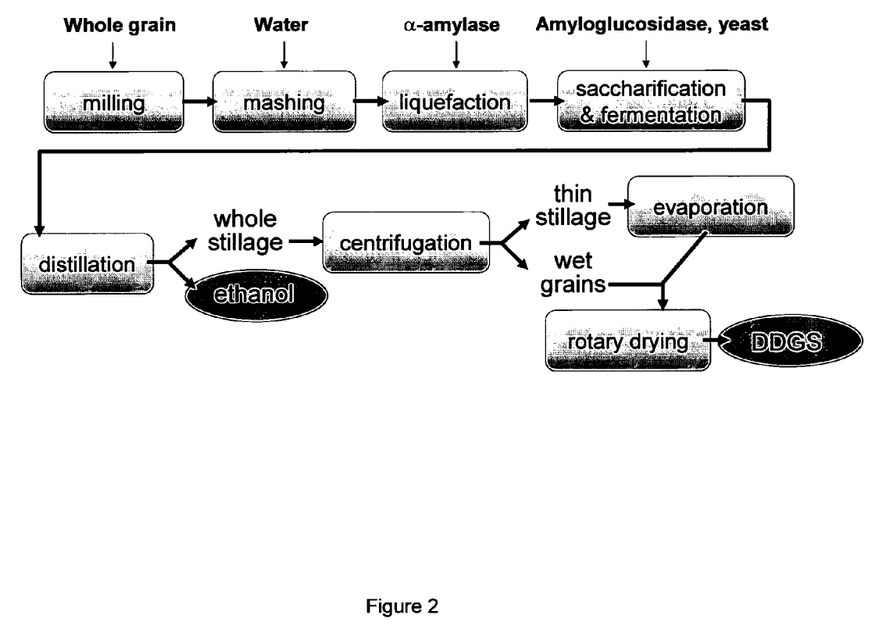
FIG. 2: Schematic representation of a conventional dry milling process of whole-grain cereals, leading to production of ethanol and distiller's dried grains and solubles (DDGS) as a co-product.

The most commonly used method for production of ethanol from cereals is the so-called dry milling process. In this process whole grains are used as an input, in contrast to the wet milling process which uses purified starch or starch-rich endosperm. The steps in conventional dry milling include (FIG. 2):

Milling: grinding of the whole grains to obtain a fine powder.

Mashing: mixing of the milled grain with water to obtain a mash or slurry.

Liquefaction: conversion of the starch to maltodextrins by addition of an alpha-amylase enzyme to the mash, by which the mash is turned into a so-called "liquefied mash".

Saccharification: conversion of the maltodextrins in the liquefied mash to glucose and maltose by addition of an amyloglucosidase or glucoamylase enzyme, by which the liquefied mash is turned into a saccharified mash. Typically, an enzyme preparation comprising endoxylanase activity is added prior to or during the saccharification. Alternatively, said enzyme preparation is added at the start of the fermentation step.

Fermentation: conversion of the glucose and maltose in the saccharified mash to ethanol and carbon dioxide through the action of a microorganism, e.g. the yeast *Saccharomyces cerevisiae*, by which the saccharified mash is turned into a fermented mash. Most often fermentation is done concurrently with saccharification in a process called simultaneous saccharification and fermentation or SSF. In some processes, liquefaction, saccharification and fermentation are performed concurrently using special enzyme blends such as STARGEN™ from the company Genencor.

Distillation: separation of ethanol from the aqueous phase. The remaining slurry consisting of aqueous phase and solids is called "whole stillage". The resulting ethanol fraction can be further dehydrated to remove residual water, or otherwise further refined.

Centrifugation: separation of the whole stillage into a solid fraction, called "distillers wet grains", and a soluble fraction, called "thin stillage".

Evaporation: concentration of the thin stillage to obtain a so-called "condensed thin stillage" or "condensed distillers solubles".

Drying: drying of the wet grains to obtain "distillers dried grains (DDG)", or drying of a mixture of distillers wet grains and condensed distillers solubles to obtain "distillers dried grains and solubles (DDGS)".

Further information on ethanol production processes be can be found in e.g. Lyons et al (1995) and Ward and Singh (2002). Recently, it is considered to also use bran or bran rich material, such as shorts, as a starting material instead or in combination with whole grains in the bioethanol production. Any of such starting materials are suitable for the purpose of the present invention.

Xylanases are sometimes used in ethanol production, and such enzymes are either added to the mash after liquefaction, during fermentation, or to the whole stillage or thin stillage. The purpose of the addition of xylanases is to reduce the viscosity of the slurries and liquids, and hence to allow increasing the gravity of slurries, facilitating pumping and to increase the efficiency of heat transfer (WO02/38786; WO2004/087889, Sorensen et al. 2006). Since viscosity in cereals is conferred by WE-AX and not by WU-AX (Meuser et al. 1986), the xylanases used in a conventional cereal based ethanol production process are either endoxylanases with a high selectivity for WE-AX, or exoxylanases, such as beta-xylosidases. This practice does not allow the solubilisation of a significant amount of water-unextractable arabinoxylans and hence does not result in the isolation of soluble arabinoxylans with an acceptable yield.

SUMMARY OF THE INVENTION

The present invention relates to a method for producing preparations comprising soluble arabinoxylans as co-products of ethanol production through fermentation of arabinoxylan-containing cereal materials, such as whole-grain cereals. In a preferred embodiment, particular endoxylanases that solubilise water-unextractable arabinoxylan are added to the insoluble fraction of the whole stillage obtained after distillation of the ethanol-containing fermented mash. The soluble arabinoxylans are subsequently recovered in the soluble fraction following separation of insoluble from soluble material. In another preferred embodiment, particular endoxylanases that solubilise water-unextractable arabinoxylan are added to the mash prepared from whole grain cereals before or during fermentation, and the soluble arabinoxylans are recovered in the soluble fraction of the whole stillage.

In a second object the present invention provides the use of the glycoside hydrolase family 11 endoxylanase Xyn2 from *Hypocrea jecorina* comprising the amino acid sequence SEQ ID No. 1 (genbank accession AAB29346) and variants thereof, comprising an amino acid sequence being at least 80%, more preferably at least 85%, most preferably at least 90%, for instance 95% homologous with SEQ ID No. 1, for the solubilisation and partial depolymerisation of arabinoxylans comprised in cereal materials.

DETAILED DESCRIPTION

DEFINITIONS

In the context of the present invention the term "endoxylanase" or "xylanase" refers to an enzyme that is able to hydrolyze the beta-1,4 glycosyl bond in non-terminal beta-D-xylopyranosyl-1,4-beta-D-xylopyranosyl units of xylan or arabinoxylan. Other names include 1,4-beta-D-xylan xylanohydrolase, 1,4-beta-xylan xylanohydrolase, beta-1,4-xylan xylanohydrolase, (1-4)-beta-xylan 4-xylanohydrolase, endo-1,4-beta-xylanase, endo-(1-4)-beta-xylanase, endo-beta-1,4-xylanase, endo-1,4-beta-D-xylanase, endo-1,4-xylanase, xylanase, beta-1,4-xylanase, beta-xylanase, beta-D-xylanase. Endoxylanases can be derived from a variety of organisms, including plant, fungal (e.g. species of *Aspergillus, Penicillium, Disporotrichum, Neurospora, Fusarium, Humicola, Trichoderma*) or bacterial species (e.g. species of *Bacillus, Aeromonas, Streptomyces, Nocardiopsis, Thermomyces*) (see for example WO92/17573, WO92/01793, WO91/19782, WO94/21785).

In the context of the present invention, "whole grain cereal" refers to the fruits from a plant of the family Poaceae, such seed containing at least the aleurone and the starchy endosperm, with or without the additional presence of pericarp, seed coat (alternatively called testa) and/or germ. The terms "bran" or "shorts" in the context of the present invention, means a cereal-derived milled fraction enriched in any or all of the tissues to be selected from aleurone, pericarp and seed coat, as compared to the corresponding intact seed.

The term 'water-unextractable arabinoxylans' (WU-AX) refers to arabinoxylan molecules, which can not be extracted from arabinoxylan-containing cereal material when suspending said material in distilled water at 4° C. for 30 minutes.

The term 'water-extractable arabinoxylans' (WE-AX) refers to arabinoxylan molecules, which are extracted from arabinoxylan-containing cereal material when suspending said material in distilled water at 4° C. for 30 minutes.

The term 'soluble arabinoxylans' refers to arabinoxylan molecules, which can be solubilised in water irrespective whether said arabinoxylan molecules are derived from the water extractable or water unextractable fraction of arabinoxylans contained in cereals.

The term endoxylanase with high selectivity for WU-AX refers to a xylanase of which the value for the substrate selectivity factor (SSF), as defined in Moers et al. (2003) and Moers et al. (2005), is at least 2 or higher. The SSF was defined by Moers et al. 2003, 2005 as the ratio of enzyme activity toward WU-AX over enzyme activity toward WE-AX. Endoxylanase activity toward WU-AX was estimated by incubation of insoluble chromogenic substrate with a range of enzyme concentrations in microtiter plates, followed by colorimetric measurement of the dye released in the supernatant. A similar approach using soluble substrate and ethanol precipitation of unhydrolysed AX fragments was used to estimate enzyme activity toward WE-AX.

The term "thermostable xylanase" refers to an enzyme whose activity at 70° C. over 1 h incubation is reduced by less than 80% compared to the optimum temperature in conditions occurring in a cereal-based mash with a dry matter content ranging from 5 to 35%. A non-limiting example of a commercially available thermostable xylanase suitable for the practice of this invention is Ecopulp™ TX200A (AB Enzymes).

The term "non-inhibited xylanase" refers to a xylanase enzyme whose activity over 1 h incubation is inhibited by less than 20% by the presence of a proteinaceous xylanase inhibitor present at concentrations typical in a regular cereal-based mash with a dry matter content ranging from 5 to 35%. A non-limiting example of a commercially available non-inhibited xylanase suitable for the practice of this invention is Grindamyl™ Powerbake™ (Danisco).

DESCRIPTION

The present invention is based on the finding that significant amounts of soluble arabinoxylans can be derived from co-products of the ethanol production when using arabinoxylan-containing cereal materials as feedstocks. Moreover, a method was worked out allowing the isolation of a preparation comprising soluble arabinoxylans from said co-products, said method being compatible with an efficient ethanol production process.

Therefore, in a first object the present invention provides a method for the co-production of ethanol and a preparation comprising soluble arabinoxylans. Said method comprises (i) the fermentation of the fermentable sugars comprised in the arabinoxylan-containing cereal material, (ii) the solubilisation of at least 15% of the water-unextractable arabinoxylans comprised in said cereal material using an enzyme preparation comprising endoxylanase activity and (iii) the isolation of a preparation comprising the solublilised arabinoxylans. Preferably, the method comprises the solubilisation of at least 25%, more preferably at least 35%, most preferably at least 40%, for instance more than 50% of the water-unextractable arabinoxylans comprised in said cereal material.

In order to obtain a sufficient yield of soluble arabinoxylans it is preferred that the arabinoxylan-containing cereal material used as raw material in the method of the present invention comprises at least 4% (w/w), more preferably at least 6% (w/w), most preferably at least 8% (w/w) of arabinoxylans. Examples of such arabinoxylan-containing cereal materials are whole grain cereals, bran enriched cereal materials, bran, shorts and the like.

In a preferred embodiment the enzyme preparation comprising endoxylanase activity used in the method of the present invention comprises an endoxylanase having a high selectivity for water unextractable arabinoxylans. Moers et al. (2005) have developed an assay to determine the selectivity of endoxylanases for WU-AX versus WE-AX, and this assay can be used to classify endoxylanases as being either specific for WU-AX or being specific for WE-AX. Endoxylanases with high specificity for WU-AX preferentially hydrolyse WU-AX, resulting in solubilisation of arabinoxylan, but leaves WE-AX and solubilised arabinoxylan relatively unaffected. Endoxylanases with high specificity for WU-AX include the glycoside hydrolase family 11 endoxylanase (classification according to http://afmb.cnrs-mrs.fr/CAZY/) from *Bacillus subtilis* (Moers et al. 2005). Other endoxylanases preferentially hydrolyse WE-AX and solubilised arabinoxylan, but have little effect on WU-AX. A typical example of the latter group of endoxylanases is the glycoside hydrolase family 10 endoxylanase (classification according to http://afmb.cnrs-mrs.fr/CAZY/) from *Aspergillus aculeatus*. In a further preferred embodiment, the said enzyme preparation comprises endoxylanase activity with high selectivity for WU-AX, which is resistant to the inhibitory action of proteinaceous xylanase inhibitors present in cereals (Gebruers et al. 2004). Examples include the glycoside hydrolase family 11 endoxylanase II (Xyn2, or alternatively called Xln2; Saarelainen et al. 1993) from *Hypocrea jecorina* (anamorph *Trichoderma longibrachiatum*, formerly *Trichoderma reesei*), which is present in the commercial product Ecopulp™ TX-200A from AB Enzymes, or an glycoside hydrolase family 11 endoxylanase from *Bacillus subtilis*, which has been developed by protein engineering to reduce the binding by xylanase inhibitors (WO0166711;

WO03020923) and which is present in the commercial product Grindamyl Powerbake™ from Danisco. The said enzyme preparation may next to endoxylanase activity, comprise additional enzyme activities selected from the group of α-L-arabinofuranosidases (which cleave off the arabinose side chains from arabinoxylan), methyl glucuronidases (which remove methyl glucuronic acid side chains), feruloyl esterases (which hydrolyse the ester bond between ferulic acid and arabinoxylan), beta-glucanases (which hydrolyse beta-glucans that can be associated with arabinoxylan) and cellulases (which hydrolyse cellulose that can be associated with arabinoxylan).

The method of the present invention is highly compatible with the ethanol production through fermentation of whole-grain cereals in a dry milling process. Such method according to the present invention typically comprises following steps:
(a) mixing of water with milled whole grain cereal or a bran-enriched milled cereal fraction to obtain a slurry;
(b) liquefaction of the slurry in the presence of an alpha amylase;
(c) saccharification of the liquefied mash in the presence of an amyloglucosidase, also named glucoamylase;
(d) fermentation of the saccharified mash with a microorganism that produces mainly ethanol as a fermentation product (Steps (b), (c), and (d) and may be performed either sequentially or simultaneously);
(e) distillation of the fermented mash to yield an ethanol fraction and a whole stillage fraction;
(f) centrifugation of the whole stillage to obtain a solids fraction (distillers wet grain) and a soluble fraction (thin stillage).

The solubilisation of the WU-AX comprised in the cereal material and the isolation of the obtained soluble arabinoxylans may be achieved through different routes. In a first embodiment the method of the present invention further comprises the following steps:
(g) resuspending the solids fraction obtained in step (f) in a suitable amount of water and adding an effective amount of said enzyme preparation containing endoxylanase activity and incubating said suspended solid fraction during an appropriate time period at an appropriate temperature, and
(h) isolating the liquid fraction from the incubated suspension obtained in step (g), said liquid fraction comprising the water soluble arabinoxylans.

Figure 3:
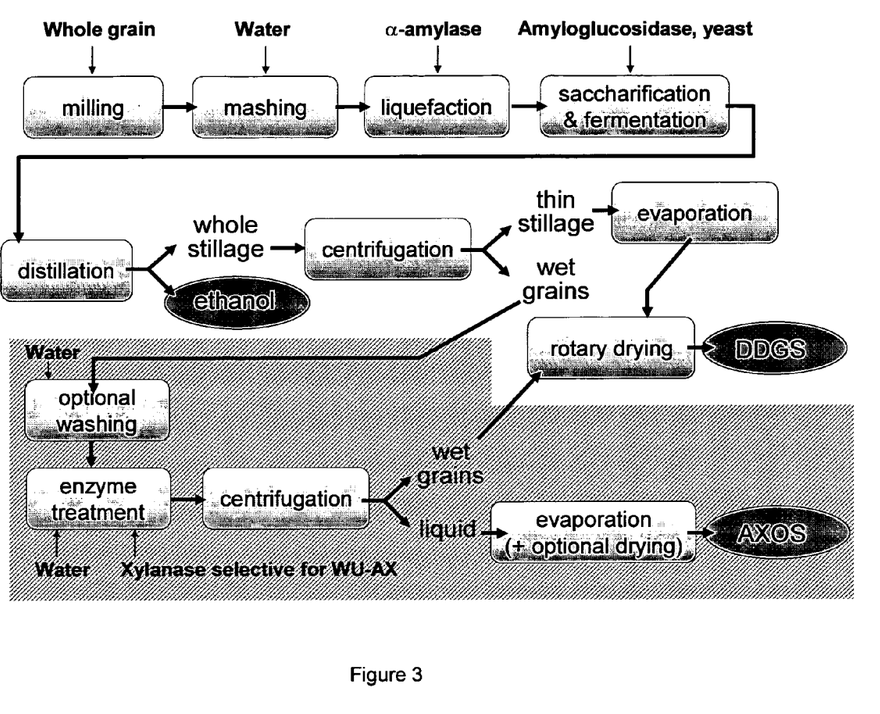
FIG. 3: Schematic representation of a novel dry milling process of whole-grain cereals, according to the present invention, leading to production of ethanol, and distiller's dried grains and solubles (DDGS) and AXOS as co-products. The steps deviating from the conventional process are indicated in the hatched zone.

The method of the present invention according to this first embodiment is further illustrated in FIG. 3, the cake-like distillers wet grain fraction obtained in step (f) is mixed with water to obtain a stirrable slurry with a ratio of dry solids to water (w:v) between 1:3 and 1:20, preferably between 1:5 and 1:10. The slurry is brought to a temperature between 40-80° C., preferably between 50-70° C., and the pH is brought to between 3 and 8, preferably between 4 and 6. The slurry is treated with an effective amount of said enzyme preparation containing endoxylanase activity. After an appropriate incubation time, between 0.5-48 h, preferably between 2-12 h, the slurry of enzyme-treated distillers wet grain is mechanically separated by centrifugation or filtration to obtain two fractions:
(f1) a liquid fraction comprising soluble arabinoxylans
(f2) a fraction enriched in insoluble solids Optionally, the distillers wet grain fraction obtained in step (f) is washed with water before the enzyme treatment in step (g). Such washing step may comprise washing with water of the solids cake in a filter, pressed filter, sieve, or centrifugal decanter, as preferred by a person skilled in the art. Preferably, the washing is performed in a counter-current flow between solids and fresh water. The solids fraction obtained after the washing step is recovered and mixed again with water as described above for the endoxylanase treatment step.

The liquid fraction (f1) is highly enriched in soluble arabinoxylans and contains on a dry matter basis at least 40% soluble arabinoxylans (w/w), preferably at least 50% soluble arabinoxylans, such as at least 60% or at least 70% soluble arabinoxylans. Optionally, this fraction is further condensed to increase the dry solids content, for instance using an evaporator that is conventionally used for condensing thin stillage. Optionally, such condensed liquid fraction (f1) can be dried, for instance using spray drying equipment, to obtain a powder that is highly enriched in soluble arabinoxylans. The condensed liquid fraction (f1) or the dried powder obtained from it can be used as food, beverage and feed ingredients.

Optionally, the liquid fraction (f1) or the condensed liquid fraction (f1) can be subjected to further purification techniques, such as for instance centrifugation, filtration, microfiltration, nanofiltration, ultrafiltration, ion exchange chromatography, size exclusion chromatography, absorption chromatography, so as to increase the purity of the soluble arabinoxylans. Optionally, the liquid fraction (f1) or the condensed liquid fraction (f1) is heated to temperatures above 80° C. to inactivate the endoxylanase or other enzymes used in the process, for instance using a jet cooker. Optionally, the liquid fraction (f1) or the condensed liquid fraction (f1) can be further used as starting material for the production of xylose and/or xylose-derived molecules such as xylitol. The fraction (f2) enriched in insoluble solids can be dried, for instance using a rotary drier, a flash drier or a ring drier, or other drying equipment that is used in the art for producing DDG or DDGS. Alternatively, the solid fraction (f2) can be mixed with condensed thin stillage of step (f) and dried to obtain a material that resembles closely DDGS and that can be used as a protein-rich animal feed or burned to recover heat energy.

In an alternative second embodiment of the invention an effective amount of said enzyme preparation containing endoxylanase activity is added to the cereal-containing slurry at one or more of the steps selected from steps (b), (c) or (d) and wherein the liquid fraction obtained in step (f), which comprises the water soluble arabinoxylans, is isolated. The method of the present invention according to this second embodiment is further illustrated in FIG. 4. The fermented mash obtained after addition of an enzyme preparation containing endoxylanase activity with high selectivity for WU-AX at one or more of the steps selected from steps (b), (c) or (d) is distilled, and the whole stillage is centrifuged or filtered to obtain two fractions:
(f3) a liquid fraction containing solubles
(f4) a fraction enriched in insoluble solids The liquid fraction (f3) is highly enriched in soluble arabinoxylans and contains on a dry matter basis at least 20% (w/w) soluble arabinoxylans, preferably at least 25% soluble arabinoxylans, most preferably at least 30% soluble arabinoxylans. Optionally, this fraction is further condensed to increase the dry solids content, for instance using an evaporator that is used in the art for condensing thin stillage. Optionally, such condensed liquid fraction (f3) can be dried, for instance using spray drying equipment, to obtain a dry powder that is highly enriched in soluble arabinoxylans. The condensed liquid fraction (f3), or the dried powder obtained from it, can be used as food, beverage or feed ingredients.

Figure 4:
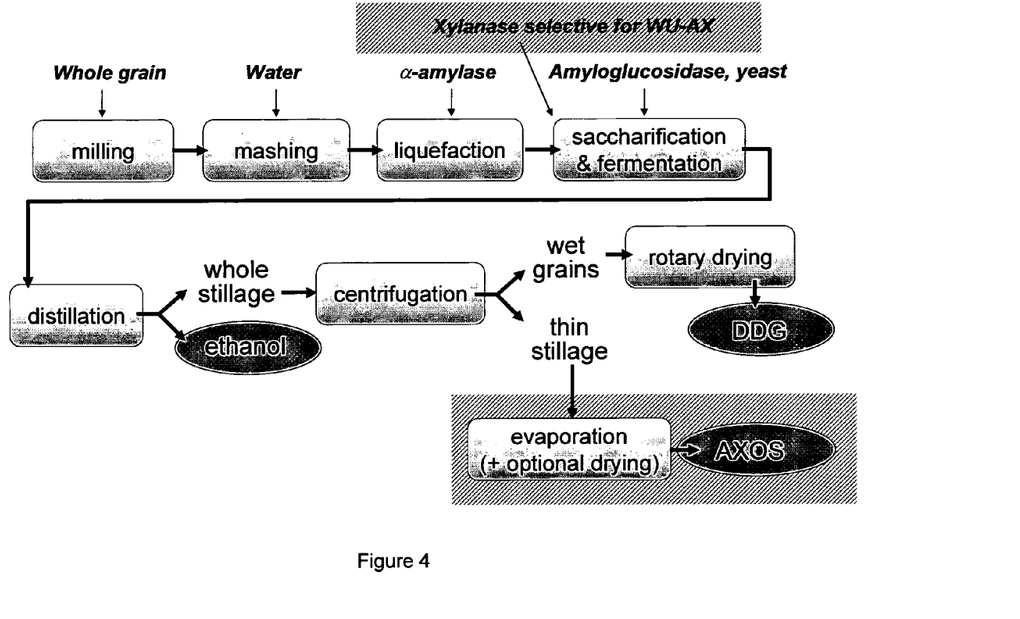
FIG. 4: Schematic representation of an alternative novel dry milling process of whole-grain cereals, according to the present invention, leading to production of ethanol, and distiller's dried grains (DDG) and AXOS as co-products. The steps deviating from the conventional process are indicated in the hatched zone.

Optionally, the liquid fraction (f3) or the condensed liquid fraction (f3) can be subjected to further purification techniques, such as for instance filtration, microfiltration, nanofiltration, ultrafiltration, ion exchange chromatography, size exclusion chromatography, absorption chromatography, so as to increase the purity of soluble arabinoxylans. Optionally, the liquid fraction (f3) or the condensed liquid fraction (f3) can be further used as starting material for the production of xylose and/or xylose-derived molecules such as xylitol or xylonic acid.

The fraction (f4) enriched in insoluble solids can be dried, for instance using a rotary drier, a flash drier or a ring drier, or other drying equipment that is used in the art for producing DDG or DDGS. Alternatively, the solid fraction (f4) can be mixed with condensed thin stillage of step (f) or step (f3) and dried to obtain a material that resembles closely DDGS and that can be used as a protein-rich animal feed.

The average degree of polymerisation (DP) of the soluble arabinoxylans comprised in the preparations obtained using the method of the present invention typically varies between 3 and 200. More preferably the average DP of the soluble arabinoxylans contained in said preparations varies between 3 and 50, even more preferably between 3 and 20, for instance between 5 and 10. Such soluble arabinoxylans-enriched preparation can be used as a food, beverage or feed additive. Such preparation can be added to a food, beverage or feed product, for instance to improve taste, mouthfeel or texture of the product, to obtain a health benefit upon ingestion of the product, and/or to improve the efficiency of food utilisation in animals.

The present invention further demonstrates that the use of a thermostable variant of the glycoside hydrolase family 11 endoxylanase II (Xyn2, or alternatively called Xln2; Saarelainen et al. 1993) from *Hypocrea jecorina* (anamorph *Trichoderna longibrachiatum*, formerly *Trichoderma reesei*), which is present in the commercial product Ecopulp™ TX-200A from AB Enzymes, is particularly suitable for solubilising and partial depolymerising of the arabinoxylans comprised in cereal material and more particularly in bran or bran enriched material. Therefore, in a second object the present invention provides the use of the glycoside hydrolase family 11 endoxylanase Xyn2 from *Hypocrea jecorina* comprising the amino acid sequence SEQ ID No. 1 (genbank accession AAB29346) and variants thereof, comprising an amino acid sequence being at least 80%, more preferable at least 85%, most preferably at least 90%, for instance 95% homologous with SEQ ID No. 1, for the solubilisation and partial depolymerisation of arabinoxylans comprised in cereal materials such as bran or bran enriched material in a process aiming at the isolation of soluble arabinoxylans. In a more preferred embodiment this second object provides the use of thermostable variants of the glycoside hydrolase family 11 endoxylanase Xyn2 from *Hypocrea jecorina*, such as the endoxylanase comprised in the commercial product Ecopulp™ TX-200A from AB Enzymes.

The present invention is further illustrated by way of the understanding non-limiting examples.

EXAMPLES

Example 1

Addition of Enzymes to Model Whole Stillage

Materials and Methods

Analytical methods. The total monosaccharide content was determined by gas-liquid chromatographic analysis of the alditol acetates after acid hydrolysis of the samples, followed by reduction with sodium borohydride and acetylation with acetic anhydride, as described by Courtin et al. (2000). The arabinoxylan (AX) content of samples was expressed as 0.88×(% arabinose+% xylose). The reducing end monosaccharide content was determined by gas-liquid chromatographic analysis of the alditol acetates after reduction with sodium borohydride, followed by acid hydrolysis and acetylation with acetic anhydride, as described by Courtin et al. (2000). The average degree of polymerisation of soluble arabinoxylans was calculated as the sum of the total xylose and arabinose content divided by the reducing end xylose content.

Determination of the activity of the enzymes. The activity of the endoxylanase preparations was measured colorimetric using Xylazyme (Megazyme, Bray, Ireland) as an insoluble substrate according to manufacturer's instructions for the assay. One unit was defined as the amount of enzyme required to yield a change in extinction at 590 nm of 1.0 under the assay conditions. The activity of endoxylanase in the commercial product Ecopulp TX-200A (AB Enzymes) was assessed in a 25 mM sodium phosphate buffer at pH 6.0 and at a temperature of 30° C. during 10 minutes. Under these conditions, the specific activity of Ecopulp TX-200A was 15,000 units/ml. The activity of the endoxylanase in a suspension in water prepared from the commercial product Grindamyl Powerbake (Danisco), was assessed in a 25 mM sodium acetate buffer at pH 4.7 and at a temperature of 30° C. during 10 minutes. Under these conditions, the specific activity of Grindamyl Powerbake was 300 units/g.

Results and Discussion

In order to investigate the fate of WU-AX in a cereal dry milling fermentation process we have analysed the presence of WU-AX and WE-AX in a reconstituted model for whole stillage. Whole stillage was reconstituted by mixing DDGS (dried distillers grain and solubles), obtained from an industrial ethanol production factory using whole-grain wheat as the basis for fermentation according to a conventional dry milling process, with demineralised water at a ratio of dry matter to water of 1:10 (w/v). The sample contained 18.6% (w/w) of arabinoxylan on dry matter basis (Table 1). The pH of the slurry was 4.0. The slurry was stirred for 15 minutes at room temperature, whereafter the slurry was centrifuged for 15 minutes at 10000 g. The supernatant and residue were lyophilised, weighed, and subjected to total and reducing end monosaccharide analysis to determine the type and content of arabinoxylan. Table 2 shows that 20% (w/w) of the arabinoxylan present in the reconstituted whole stillage slurry was recovered in the soluble fraction, which encompasses WE-AX and AX that is solubilised during the process, while 66% was recovered in the insoluble fraction, encompassing WU-AX. Hence, it is surprisingly and unexpectedly found that the majority of the arabinoxylan in the stillage of cereal dry milling is insoluble despite the use of xylanases in the process to reduce viscosity of the slurries.

In a subsequent experiment, the reconstituted whole stillage was incubated with the commercial endoxylanase preparation Powerbake Grindamyl (Danisco), containing a family 11 endoxylanase, under the following conditions:
  ratio of dry matter to water: 1:10 (w/v)
  pH: 4.1
  addition of 3.3 g Powerbake Grindamyl per kg dry matter (DM) of DDGS, corresponding to 1000 units per kg DM of DDGS
  incubation in presence of the enzyme during 3 h at 45° C. under constant stirring After the enzyme treatment, the slurry was centrifuged at 10000 g for 15 minutes to obtain a supernatant and pellet. Both the supernatant and pellet fractions were boiled during 20 minutes to inactivate the enzyme, followed by cooling, lyophilisation, and analysis of the total and reducing end monosaccharides. The fraction of arabinoxylan that ended up in the soluble fraction was increased from 20% in the absence of enzyme treatment (see Table 1) to 35% upon treatment with Powerbake Grindamyl (Table 2). The soluble fraction had an AXOS content of 19.6% (w/w) with an arabinose to xylose (A/X) ratio of 0.51 and an average degree of polymerisation of 20 (Table 2).

In a further subsequent experiment, the reconstituted whole stillage was incubated with the commercial endoxylanase preparation Ecopulp TX-200A (AB Enzymes), containing a family 11 endoxylanase, under the following conditions:
  ratio of dry matter to water: 1:10 (w/v)
  pH: 4.1
  addition of 0.5 ml Ecopulp TX-200A per kg dry matter (DM) of DDGS, corresponding to 7500 units per kg DM of DDGS
  incubation in presence of the enzyme during 3 h at 70° C. under constant stirring After the enzyme treatment, the slurry was centrifuged at 10000 g for 15 minutes to obtain a supernatant and pellet. Both the supernatant and pellet fractions were boiled during 20 minutes to inactivate the enzyme, followed by cooling, lyophilisation, and analysis of the total and reducing end monosaccharides. The fraction of arabinoxylan that ended up in the soluble fraction was increased from 20% in the absence of enzyme treatment (see Table 1) to 48% upon treatment with Ecopulp TX-200A (Table 2). The soluble fraction had an AXOS content of 25.3% (w/w) with an A/X ratio of 0.40 and an average degree of polymerisation of 8 (Table 2).

These experiments indicate that:
  i) the conventional dry milling process does not result in complete solubilisation of the available arabinoxylan despite the use of several enzyme preparations including xylanase activity;
  ii) the use of selected endoxylanases, in particular endoxylanases with a high selectivity for WU-AX, can lead to substantial solubilisation of the available arabinoxylan Example 2

Addition of Enzymes to Model Distiller's Wet Grains

Materials and Methods
See example 1
Results and Discussion
DDGS (dried distillers grain and solubles), obtained from an industrial ethanol production factory using whole-grain wheat as the basis for fermentation according to a dry milling process, was mixed with demineralised water at a ratio of dry matter to water of 1:10 (w/v). The slurry was filtered under vacuum and the filter cake was washed with demineralised water at a ratio of demineralised water volume over cake volume of 3. The washed residue was considered to be a reconstituted model for wet distiller's grain (WDG), as it contains the solid material of the whole stillage but not the solubles.

The model WDG was incubated with the commercial endoxylanase preparation Ecopulp TX-200A (AB Enzymes), containing a family 11 endoxylanase, under the following conditions:
  ratio of dry matter to water: 1:10 (w/v)
  pH: 4.1
  addition of 0.5 ml Ecopulp TX-200A per kg dry matter (DM) of WDG, corresponding to 7500 units per kg DM of WDG
  incubation in presence of the enzyme during 3 h at 70° C. under constant stirring After the enzyme treatment, the slurry was centrifuged at 10000 g for 15 minutes to obtain a supernatant and pellet. Both the supernatant and pellet fractions were boiled during 20 minutes to inactivate the enzyme, followed by cooling, lyophilisation, and analysis of the total and reducing end monosaccharides.

The fraction of arabinoxylan in the reconstituted WDG that ended up in the soluble fraction was 34% (Table 3). The soluble fraction had a surprisingly high AXOS content of 72.1% (w/w) with an A/X ratio of 0.24 and an average degree of polymerisation of 6 (Table 3).

Example 3

Addition of Enzymes to Bran-Rich Material

Materials and Methods
Wheat bran (obtained from Dossche Mills & Bakery) was destarched as follows. Wheat bran was mixed with demineralised water at a ratio of dry matter to water of 1:10 (w/v) and a thermostable amylase (Termamyl 120 L, Novozymes) was added at 1 µl per g dry mass of wheat bran. After incubation for 1.5 h at 90° C., the slurry was filtered under vacuum and the filter cake was washed with demineralised water at 80° C. a ratio of demineralised water volume over cake volume of 3. The washed residue was called destarched wheat bran.

Ecopulp® TX200A is a commercial technical grade endoxylanase preparation from AB Enzymes (Darmstadt, Germany) produced through recombinant expression of a thermophilic mutant of a *Hypocrea jecorina* (anamorph *Trichoderma longibrachiatum*, formerly *T. reesei*) GH11 endoxylanase gene. Multifect® Xylanase (MF XYL) is a commercial technical grade endoxylanase preparation from Genencor/Danisco (Palo Alto, USA) produced through recombinant expression of a *Hypocrea jecorina* (anamorph *Trichoderma longibrachiatum*, formerly *T. reesei*) GH11 endoxylanase gene. Grindamyl® H640 is a commercial food-grade endoxylanase preparation from Danisco (Copenhagen, Denmark) produced through expression in *Bacillus subtilis* of a *Bacillus subtilis* GH 11 endoxylanase gene. Frimase® B210 is a commercial food-grade endoxylanase preparation from Puratos (Groot-Bijgaarden, Belgium) produced through expression in *Bacillus subtilis* of a *Bacillus subtilis* GH 11 endoxylanase gene. Depol® 761 is a commercial food-grade endoxylanase preparation from Biocatalysts (Cardiff, UK) produced through expression in *Bacillus subtilis* of a *Bacillus subtilis* GH 11 endoxylanase gene. Onozuka® RS is a commercial endoxylanase-containing preparation from Yakult Pharmaceutical Industry (Tokyo, Japan)) prepared by non-recombinant production by *Trichoderma viride*. Shearzyme® 500L (XAA) is a commercial food-grade endoxylanase preparation from Novozymes (Bagsvaerd, Denmark) prepared by recombinant expression in *Aspergillus oryzae* of an *Aspergillus aculeatus* GH10 endoxylanase gene. Pentopan® Mono BG is a commercial food-grade endoxylanase preparation from Novozymes (Bagsvaerd, Denmark) prepared by recombinant expression in *Aspergillus oryzae* of a *Thermomyces lanuginosus* GH11 endoxylanase gene. Pentopan® 500 BG (PP 500) is a commercial food-grade endoxylanase preparation from Novozymes (Bagsvaerd, Denmark) prepared by non-recombinant production by *Humicola insolens*.

Results and Discussion
Destarched wheat bran was incubated with different commercial endoxylanase preparations under the conditions specified in Table 4. After the enzyme treatment, the slurry was filtered and the filtrate subsequently centrifuged at 10000 g for 15 minutes to obtain a clarified supernatant. The supernatant fractions were boiled during 20 minutes to inactivate the enzymes, followed by cooling, lyophilisation, and analysis of the total and reducing end monosaccharides.

As can be seen in Table 4, the highest AXOS content in the supernatant and hence the highest degree of purity was obtained upon treatment with the endoxylanase preparations from *Hypocrea jecorina* (anamorph *Trichoderma longibrachiatum*, formerly *Trichoderma reesei*), i.e. Multifect Xylanase and Ecopulp TX 200A. The highest recovery of AX was obtained with the thermostable endoxylanase from *Hypocrea jecorina*, Ecopulp TX 200A. It is concluded from this experiment that an endoxylanase preparation from *Hypocrea jecorina* is preferred for preparation of AXOS from bran-rich cereal material, and that thermostable variants of endoxylanase Xyn2 from *Hypocrea jecorina* (SEQ ID No 1) or variants thereof are particularly preferred for the solubilisation and partial depolymerisation of the arabinoxylans comprised in cereals in a procedure for the isolation of soluble arabinoxylans

REFERENCES

AOAC, 1995. Official Methods of Analysis, 16th edition. Method 990.03. Association of Official Analytical Chemists, Washington D.C., USA.

Biely, P., Vrsanska, M., Tenkanen, M., Kluepfel, D. (1997) J Biotechnol, 57: 151-166

Carvalheiro F., Esteves, M. P., Parajo J. C., Pereira, H., Girio, F. M. (2004) Production of oligosaccharides by autohydrolysis of brewery's spent grain. Bioresource Technol 91: 93-100

Courtin, C. M., Van den Broeck, H. and Delcour, J. A. (2000). Determination of reducing end sugar residues in oligo- and polysaccharides by gas liquid chromatography. Journal of Chromatography A, 866, 97-104.

Courtin, C. M. and Delcour, J. A. (2001) Relative Activity of Endoxylanases Towards Water-extractable and Water-unextractable Arabinoxylan. J. Cereal Sci, 33: 301-312.

Delcour, J. A., Van Win, H., Grobet, P. J., 1999. Distribution and structural variation of arabinoxylans in common wheat mill streams. Journal of Agricultural and Food Chemistry 47: 271-275.

Gibson, G. R. and Roberfroid M. B. (1995) Dietary modulation of the human colonic microbiota: introducing the concept of prebiotics. J. Nutr. 125: 1401-1412.

Gruppen, H., Hamer, R. J. and Voragen, A. G. J. (1992). Water-unextractable cell wall material from wheat flour. II. Fractionation of alkali-extracted polymers and comparison with water-extractable arabinoxylans. Journal of Cereal Science, 16: 53-67.

Lyon, T. P., Kesall, D. R., Murtogh, J. E. (1995) The ethanol textbook. Nothingham University Press.

Maes, C., Vangeneugden, B. and Delcour, J. A. (2004). Relative activity of two endoxylanases towards water-unextractable arabinoxylans in wheat bran. *J. Cereal Sci.,* 39: 181-186.

Meuser, F., Suckow, P. (1986) Non-starch polysaccharides. In Chemistry and Physics of Baking. Blanshard, J. M. V., Frazier, P. J., Galliard, T., Eds. Royal Society of London. London, UK. pp 43-61.

Moers K, Courtin C M, Brijs K, Delcour J A. (2003) A screening method for endo-beta-1,4-xylanase substrate selectivity. Anal Biochem. 319:73-77.

Moers, C, Celus, I., Brijs, K., Courtin, C. M., Delcour, J. A. (2005) Endoxylanase substrate selectivity determines degradation of wheat water-extractable and water-unextractable arabinoxylan. Carbohydrate Research 340: 1319-1327.

Roberfroid, M. B. (1998) Prebiotics and synbiotics: concepts and nutritional properties. Brit. J. Nutr. 80:S197-S202.

Saarelainen, R., Paloheimo, M., Fagerstrom, R., Suominen, P. L., Nevalainen, K. M. (1993) Cloning, sequencing and enhanced expression of the *Trichoderma reesei* endoxylanase II (pI 9) gene xln2. Mol. Gen. Genet. 241: 497-503.

Sorensen H R, Pedersen S, and Meyer A S (2006) Optimization, of reaction conditions for enzymatic viscosity reduction and hydrolysis of wheat arabinoxylan in an industrial ethanol fermentation residue. Biotechnol. Prog. 22: 505-513.

Swennen, K, Courtin, C. M., Lindemans G C J E, Delcour, J. A. (2006) Large-scale production and characterisation of wheat bran arabinoxylooligosaccharides. J. Sci. Food Agric. 86: 1722-1731.

Van Loo, J. A. E. (2004) Prebiotics promote good health. The basis, the potential, and the emerging evidence. J Clin Gastroenterol 38: S70-S75.

Ward, O. P. and Singh, A. (2002) Bioethanol technology: developments and perspectives. Adv. Appl. Micorbiol. 51: 53:80.

Yamada H., Itoh, K., Morishita, Y., Taniguchi, H. (1993) Structure and properties of oligosaccharides from wheat bran. Cereal Foods World 38: 490-492

TABLES

TABLE 1

Analysis of wheat whole-grain DDGS, and the soluble and insoluble fraction of DDGS. AX: arabinoxylan content expressed as % of dry matter; A/X: the arabinose to xylose ratio; avDP: average degree of polymerisation.

| Fraction | AX[a] | A/X[b] | avDP | Dry mass recovery (%) | AX recovery (%)[c] |
|---|---|---|---|---|---|
| DDGS | 18.6 | 0.66 | N.D.[d] | 100% | 100% |
| soluble fraction | 14.2 | 0.51 | 18 | 26%[e] | 20% |
| Insoluble fraction | 20.3 | 0.60 | N.D.[d] | 60% | 66% |

[a]AX = 0.88 × (% arabinose + % xylose)
[b]A/X = (% arabinose)/(% xylose)
[c]calculated as (% mass recovery) × (AX of fraction)/(AX of sample before separation)
[d]N.D. = not determined
[e]mass after lyophilisation of supernatant multiplied by (total wet mass in slurry)/(total wet mass in supernatant)

TABLE 2

Analysis of the soluble and insoluble fractions of DDGS after treatment with the endoxylanase preparations from Grindamyl Powerbake (GP) or Ecopulp Tx-200A (EP). AX: arabinoxylan content expressed as % of dry matter; A/X: the arabinose to xylose ratio; avDP: average degree of polymerisation.

| Fraction | AX[a] | A/X[b] | avDP | Dry mass recovery (%) | AX recovery (%)[c] |
|---|---|---|---|---|---|
| DDGS | 18.6 | 0.66 | N.D.[d] | 100% | 100% |
| GP soluble fraction | 19.6 | 0.51 | 20 | 30%[e] | 35% |
| GP insoluble fraction | 19.0 | 0.56 | N.D.[d] | 58% | 53% |
| EP soluble fraction | 25.3 | 0.40 | 8 | 32%[e] | 48% |
| EP insoluble fraction | 18.7 | 0.63 | N.D.[d] | 59% | 53% |

[a]AX = 0.88 × (% arabinose + % xylose)
[b]A/X = (% arabinose)/(% xylose)
[c]calculated as (% mass recovery) × (AX of fraction)/(AX of sample before separation)
[d]N.D. = not determined
[e]mass after lyophilisation of supernatant multiplied by (total wet mass in slurry)/(total wet mass in supernatant)

TABLE 3

Analysis of soluble fraction and insoluble fraction of washed DDGS after treatment with the endoxylanase preparation from Ecopulp Tx-200A (EP). AX: arabinoxylan content expressed as % of dry matter; A/X: the arabinose to xylose ratio; avDP: average degree of polymerisation.

| Fraction | AX[a] | A/X[b] | avDP | Dry mass recovery (%) | AX recovery (%)[c] |
|---|---|---|---|---|---|
| washed DDGS | 27.0 | 0.62 | N.D.[d] | 100% | 100% |
| EP soluble fraction | 72.1 | 0.24 | 6 | 13%[e] | 34% |
| EP insoluble fraction | 22.6 | 0.76 | N.D.[d] | 75% | 63% |

[a] AX = 0.88 × (% arabinose + % xylose)
[b] A/X = (% arabinose)/(% xylose)
[c] calculated as (% mass recovery) × (AX of fraction)/(AX of sample before separation)
[d] N.D. = not determined
[e] mass after lyophilisation of supernatant multiplied by (total wet mass in slurry)/(total wet mass in supernatant)

TABLE 4

Analysis of soluble fraction after treatment of destarched wheat bran with different commercial endoxylanase preparations. AX: arabinoxylan content expressed as % of dry matter; A/X: the arabinose to xylose ratio; avDP: average degree of polymerisation.

| Enzyme | Enzyme dose[a] | Incubation | AX[b] | A/X[c] | avDP[d] | Dry mass recovery (%) | AX recovery (%)[e] |
|---|---|---|---|---|---|---|---|
| Ecopulp TX200A | 1.5 μl | 3 h, 70° C. | 71% | 0.23 | 7 | 18% | 35% |
| Ecopulp TX200A | 1.5 μl | 12 h, 70° C. | 74% | 0.22 | 6 | 19% | 38% |
| Multifect Xylanase | 10 μl | 3 h, 50° C. | 70% | 0.23 | 5 | 16% | 30% |
| Onozuka RS | 3 μl | 3 h, 50° C. | 56% | 0.24 | 4 | 23% | 35% |
| Grindamyl H640 | 3 mg | 3 h, 50° C. | 61% | 0.30 | 21 | 13% | 21% |
| Grindamyl H640 | 3 mg | 12 h, 50° C. | 59% | 0.29 | 15 | 17% | 27% |
| DePol 761 | 3 mg | 3 h, 55° C. | 60% | 0.28 | 20 | 15% | 24% |
| Frimase B210 | 3 mg | 3 h, 50° C. | 57% | 0.28 | 10 | 16% | 22% |
| Pentopan Mono BG | 3 mg | 3 u, 60° C. | 64% | 0.26 | 6 | 18% | 29% |
| Pentopan 500 BG | 0.6 mg | 3 h, 60° C. | 59% | 0.28 | 4 | 19% | 30% |
| Shearzyme 500L | 1 μl | 3 h, 60° C. | 28% | 0.47 | 4 | 4.6% | 3.5% |

[a] Expressed as μl (for liquid products) or mg (for solid products) per g destarched bran
[b] AX = 0.88 × (% arabinose − 0.7 × % galactose + % xylose)
[c] A/X = (% arabinose − 0.7 × % galactose)/(% xylose)
[d] avDP = (% arabinose − 0.7 × % galactose + % xylose)/% reducing end xylose
[e] calculated as (% mass recovery) × (AX of fraction)/(AX of sample before separation)

The invention claimed is:

1. A method for the co-production of ethanol and a preparation comprising soluble arabinoxylans comprising the steps of:
   (a) mixing water with milled arabinoxylan-containing cereal material to obtain a mash,
   (b) liquefying the mash in the presence of an amylase,
   (c) saccharifying the liquefied mash in the presence of an amyloglucosidase,
   (d) fermenting the saccharified mash with a micro-organism that produces mainly ethanol as a fermentation product,
   (e) distilling the fermented mash to yield an ethanol fraction and a whole stillage fraction,
   (f) separating the whole stillage fraction to obtain a solids fraction (distillers wet grain) and a soluble fraction (thin stillage),
   wherein said method comprises the steps of:
      solubilising at least 15% of the water-unextractable arabinoxylans comprised in said cereal material, using an enzyme preparation comprising an endoxylanase having a high affinity for water-unextractable arabinoxylan, and,
      subsequently isolating the preparation comprising the soluble arabinoxylans.

2. The method according to claim 1, wherein said method comprises solubilising at least 25% of the water-unextractable arabinoxylans comprised in said cereal material.

3. The method according to claim 1, wherein the endoxylanase with a high affinity for water unextractable arabinoxylans belongs to the glycoside hydrolases family 11 endoxylanases.

4. The method according to claim 1, wherein said enzyme preparation is resistant to the inhibitory activity of proteinaceous xylanase inhibitors in cereals.

5. The method according to claim 1, wherein the steps (c) and (d), or wherein the steps (b), (c), and (d), are performed simultaneously.

6. The method according to claim 1, wherein the method further comprises the steps of:
   (g) resuspending the solids fraction obtained in step (f) in a suitable amount of water and adding an effective amount of said enzyme preparation containing endoxylanase activity and incubating said suspended solid fraction during an appropriate time period at an appropriate temperature, and
   (h) isolating the liquid fraction from the incubated suspension obtained in step (g), said liquid fraction comprising the water soluble arabinoxylans.

7. The method according to claim 6, wherein the isolated liquid fraction as obtained in step (h) is condensed.

8. The method according to claim 6, wherein the isolated liquid fraction as obtained in step (h) is dried.

9. The method according to claim 6, wherein the solids fraction obtained in step (f) is washed with water prior to resuspension and incubation of said solids fraction in the presence of an enzyme preparation with endoxylanase activity which comprises an endoxylanase, resistant to the inhibitory activity of proteinaceous xylanase inhibitors in cereals.

10. The method according to claim 1, wherein the enzyme preparation with endoxylanase activity is added to the mash at one or more of steps (b), (c) and (d) and wherein the liquid fraction comprising the water soluble arabinoxylans, obtained in step (f), is isolated.

11. The method according to claim 10, wherein said liquid fraction comprising the soluble arbinoxylans is condensed.

12. The method according to claim 1, wherein said isolated preparation comprising the soluble arabinoxylans comprises at least 20% water-soluble arabinoxylans on total dry weight.

13. The method according to claim 1, wherein said isolated preparation comprising the soluble arabinoxylans comprises arabinoxylans with an average degree of polymerization between 3 and 200.

14. The method according to claim 1, wherein said method comprises solubilising at least 40% of the water-unextractable arabinoxylans comprised in said cereal material.

15. The method according to claim 1, wherein said isolated preparation comprising the soluble arabinoxylans comprises at least 40% water-soluble arabinoxylans on total dry weight.

16. The method according to claim 1, wherein said isolated preparation comprising the soluble arabinoxylans comprises arabinoxylans with an average degree of polymerization between 5 and 20.

17. The method according to claim 1, wherein said arabinoxylan-containing cereal material comprises at least 4% (w/w) of arabinoxylans.

* * * * *